(12) United States Patent
Balbierz et al.

(10) Patent No.: US 10,098,773 B2
(45) Date of Patent: *Oct. 16, 2018

(54) RESTRICTIVE AND/OR OBSTRUCTIVE IMPLANT FOR INDUCING WEIGHT LOSS

(71) Applicant: Boston Scientific Scimed, Inc., Maple Grove, MN (US)

(72) Inventors: Daniel J. Balbierz, Redwood City, CA (US); William L. Athas, Durham, NC (US); John Lunsford, San Carlos, CA (US); William S. Eubanks, Durham, NC (US); Kevin Van Bladel, Livermore, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 122 days.

This patent is subject to a terminal disclaimer.

(21) Appl. No.: 14/740,944

(22) Filed: Jun. 16, 2015

(65) Prior Publication Data
US 2015/0272763 A1    Oct. 1, 2015

Related U.S. Application Data

(60) Continuation of application No. 13/551,504, filed on Jul. 17, 2012, which is a division of application No.
(Continued)

(51) Int. Cl.
*A61F 5/00* (2006.01)
*A61B 17/12* (2006.01)

(52) U.S. Cl.
CPC ...... *A61F 5/0086* (2013.01); *A61B 17/12009* (2013.01); *A61F 5/003* (2013.01); *A61F 5/0036* (2013.01); *A61B 2017/12018* (2013.01)

(58) Field of Classification Search
CPC ............ A61B 17/08; A61B 19/00; A61F 2/00
See application file for complete search history.

(56) References Cited

U.S. PATENT DOCUMENTS

| 1,408,865 A | 3/1922 | Codwell |
| 3,663,965 A | 5/1972 | Lee et al. |

(Continued)

FOREIGN PATENT DOCUMENTS

| CH | 680263 A5 | 7/1992 |
| EP | 0775471 | 5/1997 |

(Continued)

OTHER PUBLICATIONS

International Search Report from PCT Patent Application No. PCT/US2002/027177 dated Feb. 14, 2003.
(Continued)

*Primary Examiner* — Christine H Matthews
(74) *Attorney, Agent, or Firm* — Bookoff McAndrews, PLLC

(57) ABSTRACT

Described herein is a system for inducing weight loss in a patient, which comprises an extragastric space occupier positionable in contact with an exterior surface of a stomach wall to form an inward protrusion of wall into the stomach, and a retention device positionable in contact with the wall to retain the inward protrusion and to thereby capture the extragastric space occupier within the protrusion.

19 Claims, 7 Drawing Sheets

Related U.S. Application Data

12/765,177, filed on Apr. 22, 2010, now Pat. No. 8,241,202, which is a continuation of application No. 11/114,400, filed on Apr. 26, 2005, now Pat. No. 7,717,843.

(60) Provisional application No. 60/565,378, filed on Apr. 26, 2004.

(56) References Cited

U.S. PATENT DOCUMENTS

| | | |
|---|---|---|
| 4,134,405 A | 1/1979 | Smit |
| 4,207,890 A | 6/1980 | Mamajek et al. |
| 4,246,893 A | 1/1981 | Berson |
| 4,315,509 A | 2/1982 | Smit |
| 4,331,277 A | 5/1982 | Green |
| 4,403,604 A | 9/1983 | Wilkinson et al. |
| 4,416,267 A | 11/1983 | Garren et al. |
| 4,417,360 A | 11/1983 | Moasser |
| 4,441,215 A | 4/1984 | Kaster |
| 4,467,804 A | 8/1984 | Hardy et al. |
| 4,485,805 A | 12/1984 | Foster, Jr. |
| 4,501,264 A | 2/1985 | Rockey |
| 4,607,618 A | 8/1986 | Angelchik |
| 4,641,653 A | 2/1987 | Rockey |
| 4,648,383 A | 3/1987 | Angelchik |
| 4,694,827 A | 9/1987 | Weiner et al. |
| 4,723,547 A | 2/1988 | Kullas et al. |
| 4,747,849 A | 5/1988 | Galitier |
| 4,846,836 A | 7/1989 | Reich |
| 4,848,367 A | 7/1989 | Avant et al. |
| 4,899,747 A | 2/1990 | Garren et al. |
| 4,925,446 A | 5/1990 | Garay et al. |
| 4,946,440 A | 8/1990 | Hall |
| 4,969,896 A | 11/1990 | Shors |
| 4,997,084 A | 3/1991 | Opie et al. |
| 5,006,106 A | 4/1991 | Angelchik |
| 5,037,021 A | 8/1991 | Mills et al. |
| 5,061,275 A | 10/1991 | Wallsten et al. |
| 5,084,061 A | 1/1992 | Gau et al. |
| 5,088,979 A | 2/1992 | Filipi et al. |
| 5,163,952 A | 11/1992 | Froix |
| 5,211,658 A | 5/1993 | Clouse |
| 5,234,454 A | 8/1993 | Bangs |
| 5,246,456 A | 9/1993 | Wilkinson |
| 5,259,399 A | 11/1993 | Brown |
| 5,263,629 A | 11/1993 | Trumbull et al. |
| 5,290,217 A | 3/1994 | Campos |
| 5,306,300 A | 4/1994 | Berry |
| 5,314,473 A | 5/1994 | Godin |
| 5,327,914 A | 7/1994 | Shlain |
| 5,345,949 A | 9/1994 | Shlain |
| 5,355,897 A | 10/1994 | Pietrafitta et al. |
| 5,401,241 A | 3/1995 | Delany |
| 5,403,326 A | 4/1995 | Harrison et al. |
| 5,405,377 A | 4/1995 | Cragg |
| 5,431,673 A | 7/1995 | Summers et al. |
| 5,486,187 A | 1/1996 | Schneck |
| 5,514,176 A | 5/1996 | Bosley, Jr. |
| 5,535,935 A | 7/1996 | Vidal et al. |
| 5,542,949 A | 8/1996 | Yoon |
| 5,562,239 A | 10/1996 | Boiarski et al. |
| 5,571,116 A | 11/1996 | Bolanos et al. |
| 5,577,654 A | 11/1996 | Bishop |
| 5,593,434 A | 1/1997 | Williams |
| 5,597,107 A | 1/1997 | Knodel et al. |
| 5,609,624 A | 3/1997 | Kalis |
| 5,628,786 A | 5/1997 | Banas et al. |
| 5,630,539 A | 5/1997 | Plyley et al. |
| 5,647,526 A | 7/1997 | Green et al. |
| 5,653,743 A | 8/1997 | Martin |
| 5,662,713 A | 9/1997 | Andersen et al. |
| 5,673,841 A | 10/1997 | Schulze et al. |
| 5,674,241 A | 10/1997 | Bley et al. |
| 5,706,998 A | 1/1998 | Plyley et al. |
| 5,709,657 A | 1/1998 | Zimmon |
| 5,720,776 A | 2/1998 | Chuter et al. |
| 5,749,918 A | 5/1998 | Hogendijk et al. |
| 5,762,255 A | 6/1998 | Chrisman et al. |
| 5,771,903 A | 6/1998 | Jakobsson |
| 5,785,684 A | 7/1998 | Zimmon |
| 5,792,119 A | 8/1998 | Marx |
| 5,820,584 A | 10/1998 | Crabb |
| 5,839,639 A | 11/1998 | Sauer et al. |
| 5,848,964 A | 12/1998 | Samuels |
| 5,855,311 A | 1/1999 | Hamblin et al. |
| 5,855,601 A | 1/1999 | Bessler et al. |
| 5,856,445 A | 1/1999 | Korsmeyer |
| 5,861,036 A | 1/1999 | Godin |
| 5,868,141 A | 2/1999 | Ellias |
| 5,887,594 A | 3/1999 | LoCicero, III |
| 5,897,562 A | 4/1999 | Bolanos et al. |
| 5,910,144 A | 6/1999 | Hayashi et al. |
| 5,922,019 A | 7/1999 | Hankh et al. |
| 5,947,983 A | 9/1999 | Solar et al. |
| 5,993,473 A | 11/1999 | Chan et al. |
| 5,993,483 A | 11/1999 | Gianotti |
| 6,016,848 A | 1/2000 | Egrees |
| 6,051,015 A | 4/2000 | Maahs |
| 6,086,600 A | 7/2000 | Kortenbach |
| 6,098,629 A | 8/2000 | Johnson et al. |
| 6,102,922 A | 8/2000 | Jakobsson et al. |
| 6,113,609 A | 9/2000 | Adams |
| 6,120,534 A | 9/2000 | Ruiz |
| 6,146,416 A | 11/2000 | Andersen et al. |
| 6,159,146 A | 12/2000 | El Gazayerli |
| 6,159,238 A | 12/2000 | Killion et al. |
| 6,197,022 B1 | 3/2001 | Baker |
| 6,206,930 B1 | 3/2001 | Burg et al. |
| 6,245,088 B1 | 6/2001 | Lowery |
| 6,251,132 B1 | 6/2001 | Ravenscroft et al. |
| 6,254,642 B1 | 7/2001 | Taylor |
| 6,258,120 B1 | 7/2001 | McKenzie et al. |
| 6,264,700 B1 | 7/2001 | Kilcoyne et al. |
| 6,287,334 B1 | 9/2001 | Moll et al. |
| 6,302,917 B1 | 10/2001 | Dua et al. |
| 6,358,197 B1 | 3/2002 | Silverman et al. |
| 6,416,522 B1 | 7/2002 | Strecker |
| 6,425,916 B1 | 7/2002 | Garrison et al. |
| 6,454,785 B2 | 9/2002 | De Hoyos |
| 6,460,543 B1 | 10/2002 | Forsell |
| 6,461,366 B1 | 10/2002 | Seguin |
| 6,494,888 B1 | 12/2002 | Laufer et al. |
| 6,494,895 B2 | 12/2002 | Addis |
| 6,503,264 B1 | 1/2003 | Birk |
| 6,506,196 B1 | 1/2003 | Laufer et al. |
| 6,527,784 B2 | 3/2003 | Adams et al. |
| 6,540,789 B1 | 4/2003 | Silverman et al. |
| 6,544,291 B2 | 4/2003 | Taylor |
| 6,547,801 B1 | 4/2003 | Dargent et al. |
| 6,558,400 B2 | 5/2003 | Deem et al. |
| 6,558,429 B2 | 5/2003 | Taylor |
| 6,572,627 B2 | 6/2003 | Gabbay |
| 6,572,629 B2 | 6/2003 | Kalloo |
| 6,575,896 B2 | 6/2003 | Silverman et al. |
| 6,592,596 B1 | 7/2003 | Geitz et al. |
| 6,596,023 B1 | 7/2003 | Nunez et al. |
| 6,607,555 B2 | 8/2003 | Patterson et al. |
| 6,627,206 B2 | 9/2003 | Lloyd |
| 6,632,227 B2 | 10/2003 | Adams |
| 6,663,639 B1 | 12/2003 | Laufer et al. |
| 6,675,809 B2 | 1/2004 | Stack et al. |
| 6,676,674 B1 | 1/2004 | Dudai |
| 6,740,098 B2 | 5/2004 | Abrams et al. |
| 6,740,121 B2 | 5/2004 | Geitz et al. |
| 6,746,460 B2 | 6/2004 | Gannoe et al. |
| 6,755,869 B2 | 6/2004 | Geitz |
| 6,764,518 B2 | 7/2004 | Godin |
| 6,773,440 B2 | 8/2004 | Gannoe et al. |
| 6,773,441 B1 | 8/2004 | Laufer et al. |
| 6,790,214 B2 | 9/2004 | Kraemer et al. |
| 6,790,237 B2 | 9/2004 | Stinson |
| 6,821,285 B2 | 11/2004 | Laufer et al. |
| 6,835,200 B2 | 12/2004 | Laufer et al. |

(56) References Cited

U.S. PATENT DOCUMENTS

| | | |
|---|---|---|
| 6,845,776 B2 | 1/2005 | Stack et al. |
| 6,916,332 B2 | 7/2005 | Adams |
| 6,932,838 B2 | 8/2005 | Schwartz et al. |
| 6,960,233 B1 | 11/2005 | Berg et al. |
| 6,966,875 B1 | 11/2005 | Longobardi |
| 6,981,978 B2 | 1/2006 | Gannoe |
| 6,981,980 B2 | 1/2006 | Sampson et al. |
| 6,994,715 B2 | 2/2006 | Gannoe et al. |
| 7,011,094 B2 | 3/2006 | Rapackie et al. |
| 7,020,531 B1 | 3/2006 | Colliu et al. |
| 7,025,791 B2 | 4/2006 | Levine et al. |
| 7,033,373 B2 | 4/2006 | De La Torre et al. |
| 7,033,384 B2 | 4/2006 | Gannoe et al. |
| 7,037,344 B2 | 5/2006 | Kagan et al. |
| 7,056,305 B2 | 6/2006 | Alvarez |
| 7,066,945 B2 | 6/2006 | Hashiba et al. |
| 7,083,629 B2 | 8/2006 | Weller et al. |
| 7,090,699 B2 | 8/2006 | Geitz |
| 7,097,650 B2 | 8/2006 | Weller et al. |
| 7,097,665 B2 | 8/2006 | Stack et al. |
| 7,111,627 B2 | 9/2006 | Stack et al. |
| 7,112,186 B2 | 9/2006 | Shah |
| 7,120,498 B2 | 10/2006 | Imran et al. |
| 7,121,283 B2 | 10/2006 | Stack et al. |
| 7,146,984 B2 | 12/2006 | Stack et al. |
| 7,147,140 B2 | 12/2006 | Wukusick et al. |
| 7,152,607 B2 | 12/2006 | Stack et al. |
| 7,160,312 B2 | 1/2007 | Saadat et al. |
| 7,172,613 B2 | 2/2007 | Wazne |
| 7,175,638 B2 | 2/2007 | Gannoe et al. |
| 7,175,660 B2 | 2/2007 | Cartledge et al. |
| 7,211,114 B2 | 5/2007 | Bessler et al. |
| 7,214,233 B2 | 5/2007 | Gannoe et al. |
| 7,220,237 B2 | 5/2007 | Gannoe et al. |
| 7,220,284 B2 | 5/2007 | Kagan et al. |
| 7,223,277 B2 | 5/2007 | DeLegge |
| 7,229,428 B2 | 6/2007 | Gannoe et al. |
| 7,229,453 B2 | 6/2007 | Anderson et al. |
| 7,255,675 B2 | 8/2007 | Gertner et al. |
| 7,261,722 B2 | 8/2007 | McGuckin, Jr. et al. |
| 7,288,101 B2 | 10/2007 | Deem et al. |
| 7,306,614 B2 | 12/2007 | Weller et al. |
| 7,315,509 B2 | 1/2008 | Jeong et al. |
| 7,316,716 B2 | 1/2008 | Egan |
| 7,320,696 B2 | 1/2008 | Gazi et al. |
| 7,326,207 B2 | 2/2008 | Edwards |
| 7,335,210 B2 | 2/2008 | Smit |
| 7,347,863 B2 | 3/2008 | Rothe et al. |
| 7,347,875 B2 | 3/2008 | Levine et al. |
| 7,354,454 B2 | 4/2008 | Stack et al. |
| 7,399,304 B2 | 7/2008 | Gambale et al. |
| 7,431,725 B2 | 10/2008 | Stack et al. |
| 7,444,183 B2 | 10/2008 | Knudson et al. |
| 7,461,767 B2 | 12/2008 | Viola et al. |
| 7,470,251 B2 | 12/2008 | Shah |
| 7,485,142 B2 | 2/2009 | Milo |
| 7,503,922 B2 | 3/2009 | Deem et al. |
| 7,520,884 B2 | 4/2009 | Swanstrom et al. |
| 7,575,586 B2 | 8/2009 | Berg et al. |
| 7,628,821 B2 | 12/2009 | Stack et al. |
| 7,662,161 B2 | 2/2010 | Briganti et al. |
| 7,670,279 B2 | 3/2010 | Gertner |
| 7,674,271 B2 | 3/2010 | Bjerken |
| 7,717,843 B2 | 5/2010 | Balbierz et al. |
| 7,753,928 B2 | 7/2010 | Torre et al. |
| 7,803,195 B2 | 9/2010 | Levy et al. |
| 8,066,780 B2 | 11/2011 | Chen et al. |
| 8,147,561 B2 | 4/2012 | Binmoeller |
| 8,241,202 B2 | 8/2012 | Balbierz et al. |
| 2001/0011543 A1 | 8/2001 | Forsell |
| 2001/0020189 A1 | 9/2001 | Taylor |
| 2001/0020190 A1 | 9/2001 | Taylor |
| 2001/0021796 A1 | 9/2001 | Silverman et al. |
| 2001/0044595 A1 | 11/2001 | Reydel et al. |
| 2002/0022851 A1 | 2/2002 | Kalloo et al. |
| 2002/0055757 A1 | 5/2002 | Torre et al. |
| 2002/0072761 A1 | 6/2002 | Abrams et al. |
| 2002/0082621 A1 | 6/2002 | Shurr et al. |
| 2002/0099439 A1 | 7/2002 | Schwartz et al. |
| 2002/0183767 A1 | 12/2002 | Adams et al. |
| 2002/0183768 A1 | 12/2002 | Deem et al. |
| 2003/0009236 A1 | 1/2003 | Godin |
| 2003/0040804 A1 | 2/2003 | Stack et al. |
| 2003/0040808 A1 | 2/2003 | Stack et al. |
| 2003/0065359 A1 | 4/2003 | Weller et al. |
| 2003/0093117 A1 | 5/2003 | Saadat et al. |
| 2003/0109892 A1 | 6/2003 | Deem et al. |
| 2003/0120289 A1 | 6/2003 | McGuckin, Jr. et al. |
| 2003/0191476 A1 | 10/2003 | Smit |
| 2003/0199989 A1 | 10/2003 | Stack et al. |
| 2003/0199990 A1 | 10/2003 | Stack et al. |
| 2003/0199991 A1 | 10/2003 | Stack et al. |
| 2003/0208209 A1 | 11/2003 | Gambale et al. |
| 2003/0220660 A1 | 11/2003 | Kortenbach et al. |
| 2004/0030347 A1 | 2/2004 | Gannoe et al. |
| 2004/0044357 A1 | 3/2004 | Gannoe et al. |
| 2004/0044364 A1 | 3/2004 | DeVries et al. |
| 2004/0049209 A1 | 3/2004 | Benchetrit |
| 2004/0082963 A1 | 4/2004 | Gannoe et al. |
| 2004/0088023 A1 | 5/2004 | Imran et al. |
| 2004/0092892 A1 | 5/2004 | Kagan et al. |
| 2004/0092974 A1 | 5/2004 | Gannoe et al. |
| 2004/0093091 A1 | 5/2004 | Gannoe et al. |
| 2004/0098043 A1 | 5/2004 | Trout |
| 2004/0107004 A1 | 6/2004 | Levine et al. |
| 2004/0117031 A1 | 6/2004 | Stack et al. |
| 2004/0138761 A1 | 7/2004 | Stack et al. |
| 2004/0143342 A1 | 7/2004 | Stack et al. |
| 2004/0148034 A1 | 7/2004 | Kagan et al. |
| 2004/0153167 A1 | 8/2004 | Stack et al. |
| 2004/0158331 A1 | 8/2004 | Stack et al. |
| 2004/0162568 A1 | 8/2004 | Saadat et al. |
| 2004/0172141 A1 | 9/2004 | Stack et al. |
| 2004/0172142 A1 | 9/2004 | Stack et al. |
| 2004/0210243 A1 | 10/2004 | Gannoe et al. |
| 2004/0215216 A1 | 10/2004 | Gannoe et al. |
| 2004/0220682 A1 | 11/2004 | Levine et al. |
| 2004/0225183 A1 | 11/2004 | Michlitsch et al. |
| 2004/0225305 A1 | 11/2004 | Ewers et al. |
| 2004/0236419 A1 | 11/2004 | Milo |
| 2004/0243152 A1 | 12/2004 | Taylor et al. |
| 2004/0243223 A1 | 12/2004 | Kraemer et al. |
| 2005/0004430 A1 | 1/2005 | Lee et al. |
| 2005/0004681 A1 | 1/2005 | Stack et al. |
| 2005/0033326 A1 | 2/2005 | Briganti et al. |
| 2005/0049718 A1 | 3/2005 | Dann et al. |
| 2005/0075654 A1 | 4/2005 | Kelleher |
| 2005/0080444 A1 | 4/2005 | Kraemer et al. |
| 2005/0085787 A1 | 4/2005 | Laufer et al. |
| 2005/0096673 A1 | 5/2005 | Stack et al. |
| 2005/0096750 A1 | 5/2005 | Kagan et al. |
| 2005/0149114 A1 | 7/2005 | Cartledge et al. |
| 2005/0159769 A1 | 7/2005 | Alverdy |
| 2005/0177181 A1 | 8/2005 | Kagan et al. |
| 2005/0192599 A1 | 9/2005 | Demarais |
| 2005/0240279 A1 | 10/2005 | Kagan et al. |
| 2005/0247320 A1 | 11/2005 | Stack et al. |
| 2005/0250980 A1 | 11/2005 | Swanstrom et al. |
| 2005/0251158 A1 | 11/2005 | Sadat et al. |
| 2005/0251162 A1 | 11/2005 | Rothe et al. |
| 2005/0256533 A1 | 11/2005 | Roth et al. |
| 2005/0256587 A1 | 11/2005 | Egan |
| 2005/0261712 A1 | 11/2005 | Balbierz et al. |
| 2005/0267499 A1 | 12/2005 | Stack et al. |
| 2005/0267596 A1 | 12/2005 | Chen et al. |
| 2006/0015006 A1 | 1/2006 | Laurence et al. |
| 2006/0020278 A1 | 1/2006 | Burnett et al. |
| 2006/0058829 A1 | 3/2006 | Sampson et al. |
| 2006/0151568 A1 | 7/2006 | Weller et al. |
| 2006/0155259 A1 | 7/2006 | MacLay |
| 2006/0155311 A1 | 7/2006 | Hashiba et al. |
| 2006/0178560 A1 | 8/2006 | Saadat et al. |
| 2006/0195139 A1 | 8/2006 | Gertner |
| 2006/0253142 A1 | 11/2006 | Bjerken |

(56) References Cited

U.S. PATENT DOCUMENTS

| | | |
|---|---|---|
| 2006/0271076 A1 | 11/2006 | Weller et al. |
| 2006/0282095 A1 | 12/2006 | Stokes et al. |
| 2006/0287734 A1 | 12/2006 | Stack et al. |
| 2007/0010864 A1 | 1/2007 | Dann et al. |
| 2007/0032800 A1 | 2/2007 | Oritz et al. |
| 2007/0043384 A1 | 2/2007 | Oritz et al. |
| 2007/0055292 A1 | 3/2007 | Oritz et al. |
| 2007/0060932 A1 | 3/2007 | Stack et al. |
| 2007/0149994 A1 | 6/2007 | Sosnowski et al. |
| 2007/0175488 A1 | 8/2007 | Cox et al. |
| 2007/0191870 A1 | 8/2007 | Baker et al. |
| 2007/0191871 A1 | 8/2007 | Baker et al. |
| 2007/0198074 A1 | 8/2007 | Dann et al. |
| 2007/0219571 A1 | 9/2007 | Balbierz et al. |
| 2007/0239284 A1 | 10/2007 | Skerven et al. |
| 2007/0260327 A1 | 11/2007 | Case et al. |
| 2007/0276432 A1 | 11/2007 | Stack et al. |
| 2008/0033574 A1 | 2/2008 | Bessler et al. |
| 2008/0065122 A1 | 3/2008 | Stack et al. |
| 2008/0116244 A1 | 5/2008 | Rethy et al. |
| 2008/0190989 A1 | 8/2008 | Crews et al. |
| 2008/0195226 A1 | 8/2008 | Williams et al. |
| 2008/0208355 A1 | 8/2008 | Stack et al. |
| 2008/0208356 A1 | 8/2008 | Stack et al. |
| 2008/0269797 A1 | 10/2008 | Stack et al. |
| 2008/0294179 A1 | 11/2008 | Balbierz et al. |
| 2009/0018558 A1 | 1/2009 | Laufer et al. |
| 2009/0024143 A1 | 1/2009 | Crews et al. |
| 2009/0030284 A1 | 1/2009 | Cole et al. |
| 2009/0125040 A1 | 5/2009 | Hambley et al. |
| 2009/0171383 A1 | 7/2009 | Cole et al. |
| 2009/0177215 A1 | 7/2009 | Stack et al. |
| 2009/0236388 A1 | 9/2009 | Cole et al. |
| 2009/0236389 A1 | 9/2009 | Cole et al. |
| 2009/0236390 A1 | 9/2009 | Cole et al. |
| 2009/0236391 A1 | 9/2009 | Cole et al. |
| 2009/0236392 A1 | 9/2009 | Cole et al. |
| 2009/0236394 A1 | 9/2009 | Cole et al. |
| 2009/0236396 A1 | 9/2009 | Cole et al. |
| 2009/0236397 A1 | 9/2009 | Cole et al. |
| 2009/0236398 A1 | 9/2009 | Cole et al. |
| 2009/0236400 A1 | 9/2009 | Cole et al. |
| 2009/0236401 A1 | 9/2009 | Cole et al. |
| 2009/0299487 A1 | 12/2009 | Stack et al. |
| 2010/0016988 A1 | 1/2010 | Stack et al. |
| 2010/0100109 A1 | 4/2010 | Stack et al. |
| 2013/0023727 A1* | 1/2013 | Balbierz et al. ............ 600/37 |

FOREIGN PATENT DOCUMENTS

| | | |
|---|---|---|
| EP | 1492478 | 1/2005 |
| EP | 1602336 | 12/2005 |
| FR | 2768324 | 3/1999 |
| JP | 09-168597 | 6/1997 |
| WO | WO 91/01117 | 2/1991 |
| WO | WO 97/47231 | 12/1997 |
| WO | WO 00/12027 | 3/2000 |
| WO | WO 00/32137 | 6/2000 |
| WO | WO 00/78227 | 12/2000 |
| WO | WO 01/41671 | 6/2001 |
| WO | WO 01/45485 | 6/2001 |
| WO | WO 01/49359 | 7/2001 |
| WO | WO 01/66018 | 9/2001 |
| WO | WO 01/85034 | 11/2001 |
| WO | WO 01/89393 | 11/2001 |
| WO | WO 02/060328 | 8/2002 |
| WO | WO 03/017882 | 3/2003 |
| WO | WO 03/086246 | 10/2003 |
| WO | WO 03/086247 | 10/2003 |
| WO | WO 03/090633 | 11/2003 |
| WO | WO 03/094784 | 11/2003 |
| WO | WO 03/094785 | 11/2003 |
| WO | WO 03/099137 | 12/2003 |
| WO | WO 04/019765 | 3/2004 |
| WO | WO 04/019765 A | 3/2004 |
| WO | WO 04/019787 | 3/2004 |
| WO | WO 04/032760 | 4/2004 |
| WO | WO 04/037064 | 5/2004 |
| WO | WO 04/041133 | 5/2004 |
| WO | WO 04/064680 | 8/2004 |
| WO | WO 04/064685 | 8/2004 |
| WO | WO 04/080336 | 9/2004 |
| WO | WO 04/110285 | 12/2004 |
| WO | WO 05/037152 | 4/2005 |
| WO | WO 05/079673 | 9/2005 |
| WO | WO 05/096991 | 10/2005 |
| WO | WO 05/105003 | 11/2005 |
| WO | WO 06/016894 | 2/2006 |
| WO | WO 06/055365 | 5/2006 |
| WO | WO 06/127593 | 11/2006 |
| WO | WO 07/041598 | 4/2007 |
| WO | WO 08/030403 | 3/2008 |
| WO | WO 08/033409 | 3/2008 |
| WO | WO 08/033474 | 3/2008 |
| WO | WO 08/141288 | 11/2008 |
| WO | WO 09/011881 | 1/2009 |
| WO | WO 09/011882 | 1/2009 |
| WO | WO 09/086549 | 7/2009 |
| WO | WO 09/117533 | 9/2009 |
| WO | WO 10/054399 | 5/2010 |
| WO | WO 10/054404 | 5/2010 |

OTHER PUBLICATIONS

International Search Report from PCT Patent Application No. PCT/US2003/004378 dated Aug. 13, 2003.
International Search Report from PCT Patent Application No. PCT/US2003/033605 dated Mar. 29, 2004.
International Search Report from PCT Patent Application No. PCT/US2003/033606 dated Mar. 29, 2004.
International Search Report from PCT Patent Application No. PCT/US2003/004449 dated Aug. 13, 2003.
International Search Report from PCT Patent Application No. PCT/US2004/006695 dated Sep. 8, 2004.
International Search Report from PCT Patent Application No. PCT/US2004/033007 dated Feb. 9, 2005.
International Search Report from PCT Patent Application No. PCT/US2005/014372 dated Jul. 28, 2005.
International Search Report from PCT Patent Application No. PCT/US2006/019727 dated Apr. 19, 2007.
International Search Report from PCT Patent Application No. PCT/US2006/038684 dated Feb. 14, 2007.
International Search Report from PCT Patent Application No. PCT/US2007/019227 dated Feb. 20, 2008.
International Search Report from PCT Patent Application No. PCT/US2007/019833 dated Feb. 20, 2008.
International Search Report from PCT Patent Application No. PCT/US2007/019940 dated Mar. 14, 2008.
International Search Report from PCT Patent Application No. PCT/US2008/008726 dated Oct. 16, 2008.
International Search Report from PCT Patent Application No. PCT/US2008/008729 dated Aug. 18, 2009.
International Search Report from PCT Patent Application No. PCT/US2008/063440 dated Aug. 1, 2008.
International Search report and Written Opinion for PCT application PCT/US2008/088581, dated Feb. 26, 2009, 9 pages (2009).
International Search Report from PCT Patent Application No. PCT/US2009/037586 dated Sep. 28, 2009.
International Search Report from PCT Patent Application No. PCT/US2009/063925 dated Jan. 12, 2010.
International Search Report from PCT Patent Application No. PCT/US2009/063930 dated Jan. 12, 2010.
Felsher, et al., "Mucosal apposition in endoscopic suturing", Gastrointestinal Endoscopy, vol. 58, No. 6, pp. 867-870, (2003).
Stecco, et al., "Trans-oral plication formation and gastric implant placement in a canine model", Stecco Group, San Jose and Barosense, Inc., Redwood City, CA (2004).

(56) References Cited

OTHER PUBLICATIONS

Stecco, et al. "Safety of a gastric restrictive implant in a canine model", Stecco group, San Jose amd Barosense, Inc., Redwood City, CA (2004).

* cited by examiner

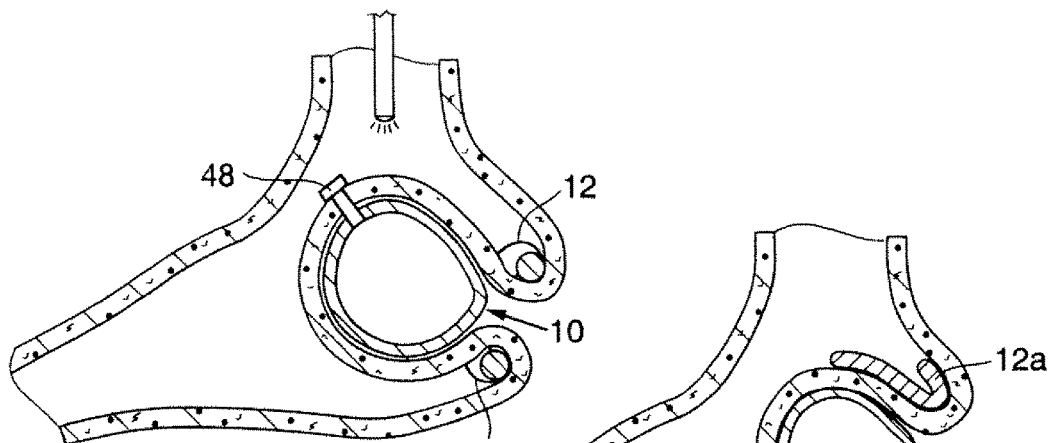
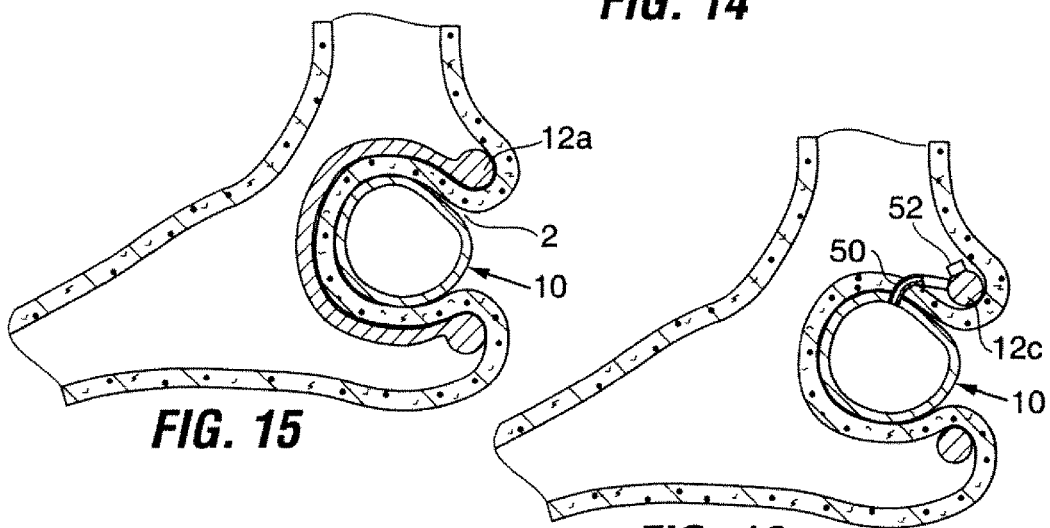
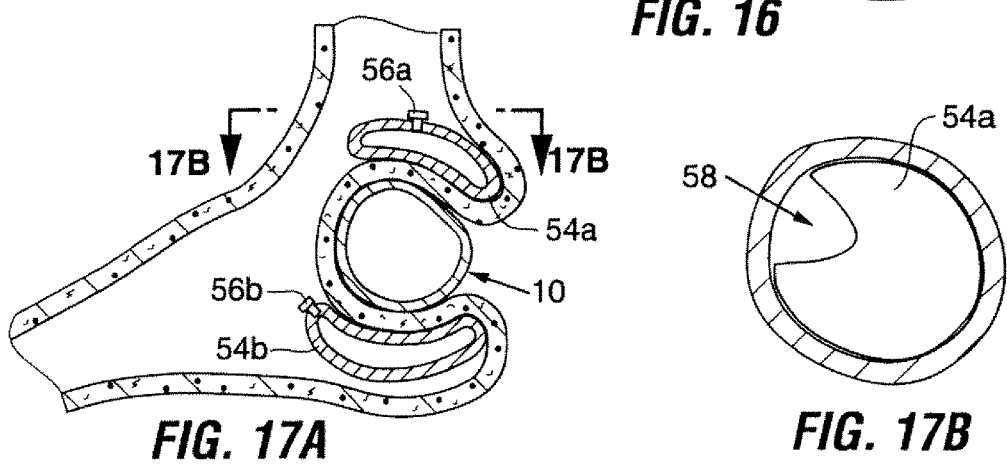

US 10,098,773 B2

RESTRICTIVE AND/OR OBSTRUCTIVE IMPLANT FOR INDUCING WEIGHT LOSS

PRIORITY CLAIM

This application is a continuation of U.S. patent application Ser. No. 13/551,504, filed Jul. 17, 2012, which is a divisional of U.S. patent application Ser. No. 12/765,177, filed Apr. 22, 2010, now U.S. Pat. No. 8,241,202, which is a continuation of U.S. patent application Ser. No. 11/114,400, filed Apr. 26, 2005, now U.S. Pat. No. 7,717,843, which claims the benefit of U.S. Provisional Patent Application No. 60/565,378, filed Apr. 26, 2004, each of which are incorporated herein by reference in their entirety.

FIELD OF THE INVENTION

The present invention relates generally to the field of implants for inducing weight loss in patients, and specifically to devices and methods for reducing the effective volume of a patient's stomach and or creating restrictions to slow passage of food into the stomach.

BACKGROUND OF THE INVENTION

An anatomical view of a human stomach S and associated features is shown in FIG. 1A. The esophagus E delivers food from the mouth to the proximal portion of the stomach S. The z-line or gastro-esophageal junction Z is the irregularly-shaped border between the thin tissue of the esophagus and the thicker tissue of the stomach wall. The gastro-esophageal junction region G is the region encompassing the distal portion of the esophagus E, the z-line, and the proximal portion of the stomach S.

Stomach S includes a fundus F at its proximal end and an antrum A at its distal end. Antrum A feeds into the pylorus P which attaches to the duodenum D, the proximal region of the small intestine. Within the pylorus P is a sphincter that prevents backflow of food from the duodenum D into the stomach. The middle region of the small intestine, positioned distally of the duodenum D, is the jejunum J.

FIG. 1B illustrates the tissue layers forming the stomach wall. The outermost layer is the serosal layer or "serosa" S and the innermost layer, lining the stomach interior, is the mucosal layer or "mucosa" MUC. The submucosa SM and the multi-layer muscularis M lie between the mucosa and the serosa.

Prior art treatments for obesity range from diet and medication to highly invasive surgical procedures. Some of the more successful surgical procedures are the vertical banded gastroplexy or the proximal gastric pouch with a Roux-en-Y anastomosis. However, known complications are present with each of these procedures. More successful and less invasive options are desired.

A less invasive prior art treatment for obesity includes implantation of a gastric balloon delivered into the stomach via the esophagus. The balloon is an obstructive device—it prevents overeating by occupying volume within the stomach. Although implantation of a gastric balloon is less invasive than other surgical procedures, gastric balloons can migrate down the GI tract, causing obstruction and thus necessitating removal.

BRIEF DESCRIPTION OF THE DRAWINGS

FIGS. 10-12A are perspective views of alternative configurations for obstructive implants.

FIG. 13G is an implantation step that is an alternative to the step shown in FIG. 13F.

FIG. 14 is a cross-section view of a stomach illustrating use of a force-distributing retention band with an obstructive implant.

FIG. 15 is a cross-section view of a stomach illustrating use of an alternative force-distributing retention band with an obstructive implant.

FIGS. 16 through 18 are cross-section views of a stomach illustrating alternate retention methods for obstructive implants.

DETAILED DESCRIPTION OF THE DRAWINGS

Figure 2:
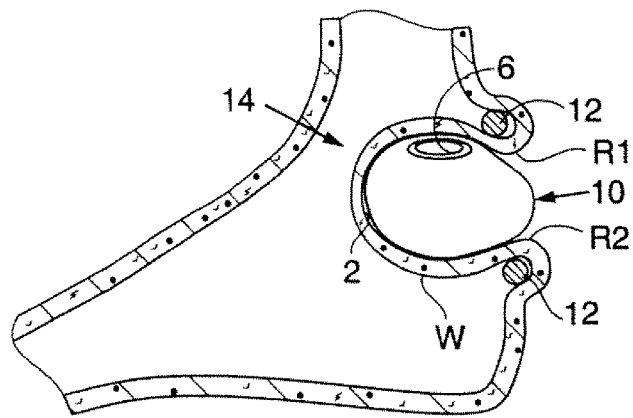
FIG. 2 is a cross-section view of a stomach illustrating positioning of an obstructive implant.

Referring to FIG. 2, an obstructive implant 10 includes a body positioned against the exterior of the stomach wall W. The implant occupies stomach volume by causing a portion of the stomach wall W to bulge into the interior volume of the stomach, thus reducing the effective volume of the stomach interior and reducing stomach capacity. Because the implant 10 is positioned outside the stomach, it cannot migrate into the intestinal tract creating obstructions. A retention band 12 is positioned within the stomach encircling a portion of the wall W so as to retain the implant 10 within pocket 2 as shown. The retention band 12 may be a ring that is elastic or inelastic, flexible or fairly rigid. The diameter of the retention band 12 may be adjustable if desired. The retention band 12 is preferably proportioned such that in the event the band becomes free within the stomach, it can pass through the intestinal system without incident. Thus, the retention device is preferably of a size that will not on its own to occupy sufficient space within the stomach to create feelings of satiety, but that relies on the extragastric implant 10 to reduce stomach capacity. Nonetheless, in alternate embodiments the retention band 12 may also perform a space-occupying function, and/or a restrictive and/or obstructive function.

Various positions for the implant are illustrated in the drawings. Depending on the size and positioning of the implant, it may function as an obstructive device, a restrictive device, or both. In some embodiments, the implant may have an expanded volume in the range of approximately 200-700 cc, sufficient to cause the inwardly-protruding pocket 2 to fill a portion of the stomach, thereby causing the patient to feel full and thus limiting food intake. In FIG. 2, the implant is positioned to function as an obstructive device (i.e. to occupy space so as to reduce effective stomach volume), but also to create a restriction 14 in the stomach. The restriction 14 is a narrowed region of the stomach, which slows the rate at which food can descend from the esophagus into the stomach. Food may accumulate in the region above the restriction, causing the patient to experience feelings of satiety and thus limiting food intake, and/or limiting the amount of food a patient can consume at one time.

Figure 3:
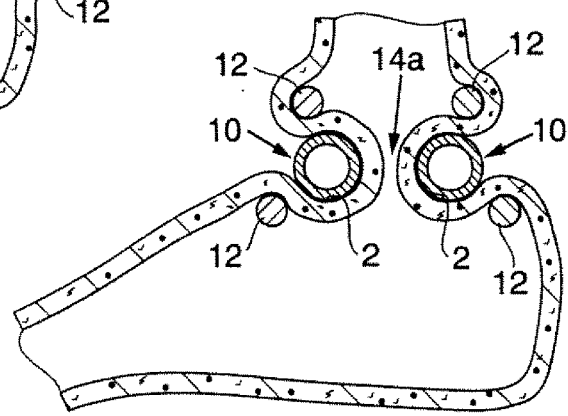
FIG. 3 is a cross-section view of a stomach illustrating positioning of two obstructive implants.

FIG. 3 shows a pair of implants 10 and a pair of retention bands 12 positioned in the proximal stomach to create a restriction 14a. This restriction 14a may also minimize reflux and thus function as treatment for patients suffering from gastro-intestinal reflux disease (GERD).

Figure 1A:
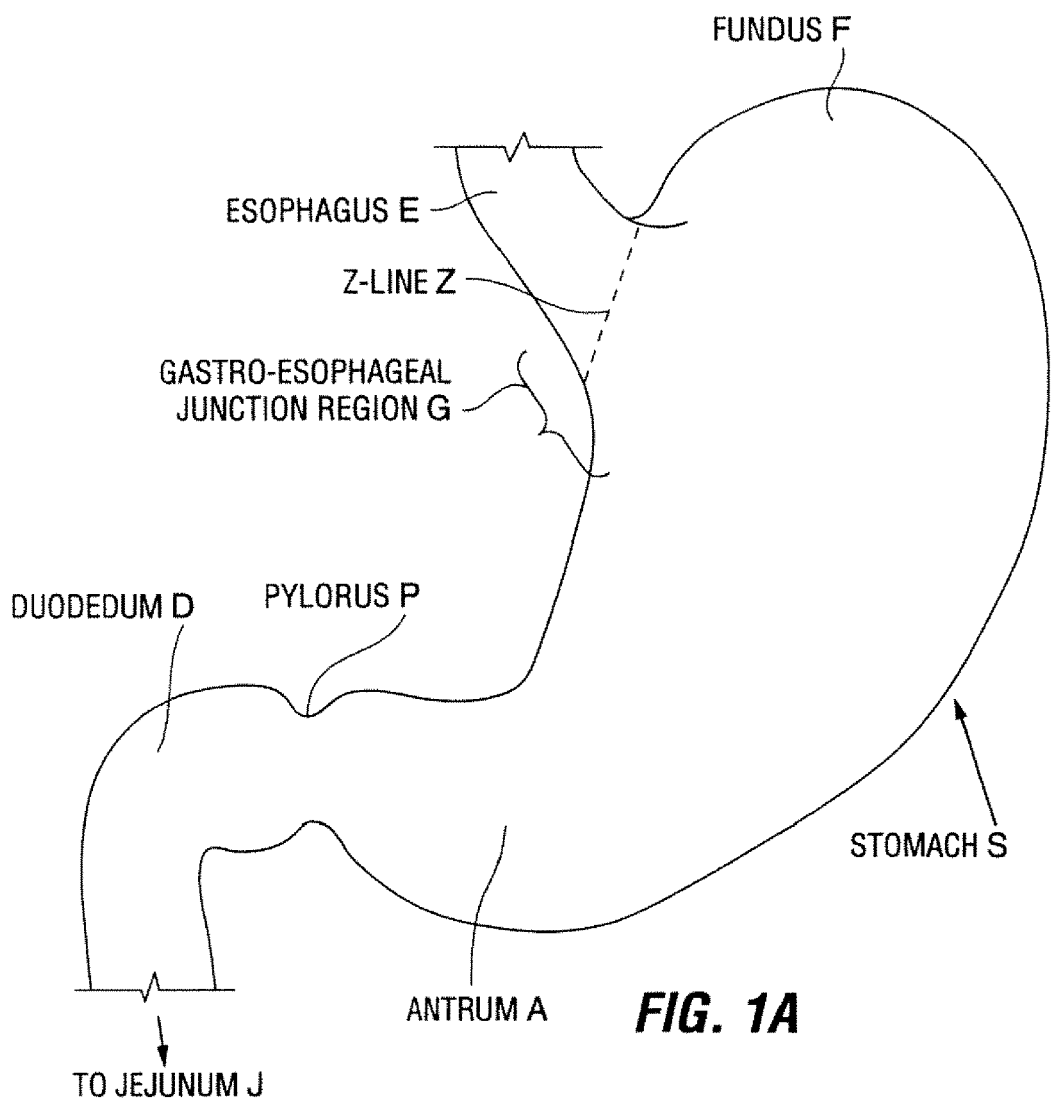
FIG. 1A is a schematic illustration of a human stomach and a portion of the small intestine.
Figure 1B:
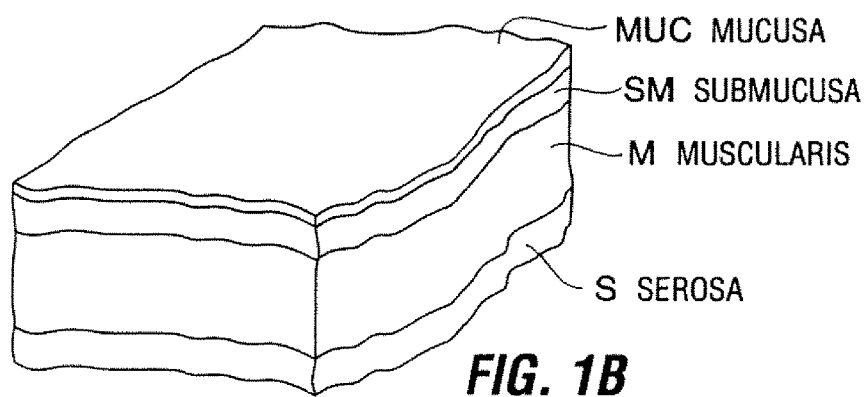
FIG. 1B is a cross-sectional perspective view of a portion of a stomach wall, illustrating the layers of tissue forming the wall.
Figure 4:
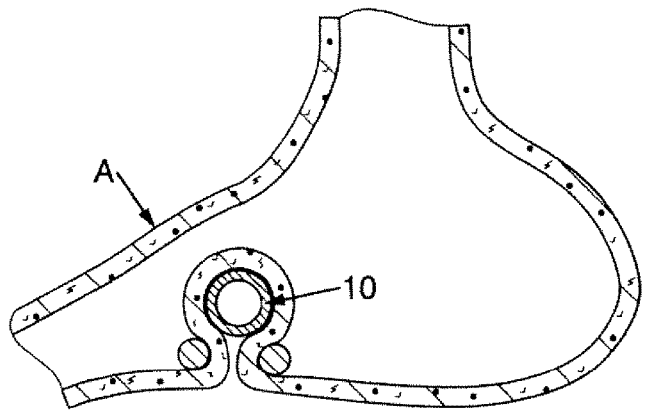
FIG. 4 is a cross-section view of a stomach illustrating positioning of an obstructive implant in the antral region of the stomach.
Figure 5:
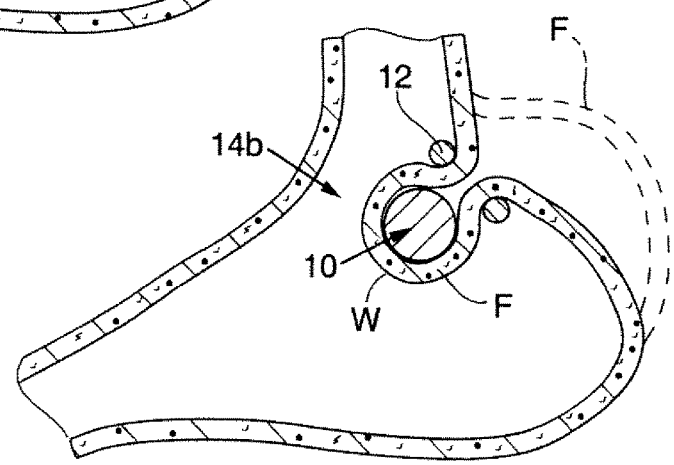
FIG. 5 is a cross-section view of a stomach illustrating positioning of an obstructive implant in the fundal region of the stomach.

FIG. 4 illustrates that the implant 10 may be positioned in the antrum A. It may similarly be positioned at the pylorus P (see FIG. 1A). Alternatively, the implant 10 may be positioned in the fundus F as shown in FIG. 5 again creating an obstruction as well as an (optional) restriction 14b in the proximal stomach. The original position of the wall of the fundus F is illustrated in dashed lines.

Figure 6:
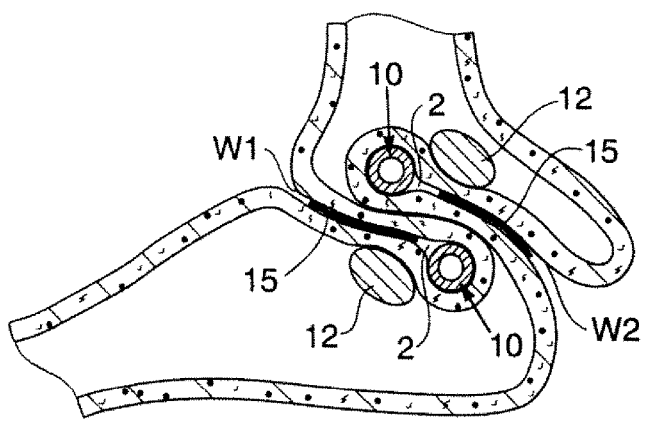
FIG. 6 is a cross-section view of a stomach illustrating alternative positioning of two obstructive implants
Figure 7:
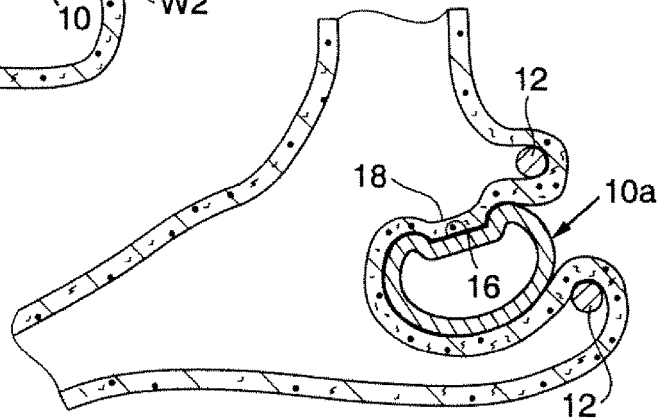
FIG. 7 is a cross-section view of a stomach illustrating positioning of an irregularly-shaped obstructive implant.
Figure 8:
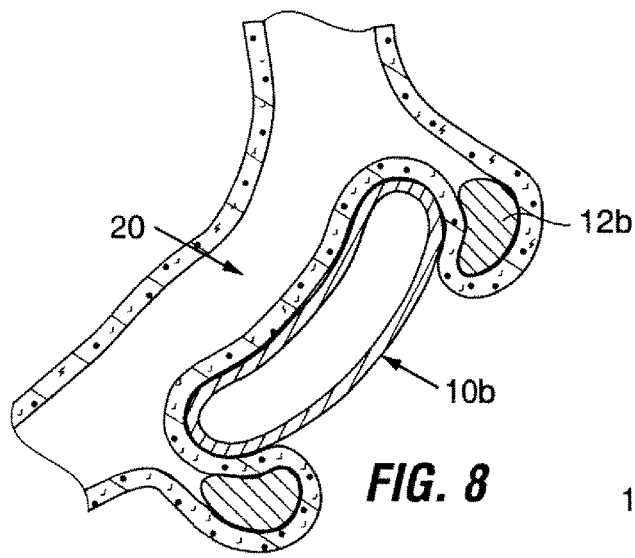
FIG. 8 is a cross-section view of a stomach illustrating positioning of an elongate obstructive implant.

FIG. 6 illustrates that a pair of implants 10 may be positioned against regions of stomach wall W1, W2 on opposite sides of the stomach. These implants are retained in their respective pockets 2 using a single retention band 12 encircling both regions of wall W1, W2 to create an obstruction within the stomach and which creates restricted flow paths on opposite sides of the obstruction.

The configuration illustrated in FIG. 6 is particularly advantageous in that it relies in part on adhesion of the serosal tissue lining the outer surface of the stomach. It has been found that serosal tissue layers can adhere to form relatively strong bonds when held in apposition to one another. Other embodiments including, but not limited to, the FIGS. 2-5, 7 and 8 embodiments may be modified to allow the retention band to retain regions of serosal tissue into contact with one another such that over time the serosal tissue will adhere as a permanent means for retaining the implant 10. For example, if such a modification was made to the FIG. 2 embodiment, the regions R1, R2 of stomach wall would be drawn into contact with one other, and retention band 12 would retain that contact until the serosal layers adhered to one another. At that time, the retention band (or other retention devices such as sutures, staples, etc.) could be removed from the stomach, such that no device remained in the stomach interior, and the implant remained in the protrusion formed against the exterior stomach wall. It may be further desirable in such embodiments to inflate the implant during a later procedure performed after the serosal layers have adhered to one another. In such embodiments, inflation may be carried out using a needle introduced into the stomach, used to pierce the stomach wall, and then passed into an inflation port (e.g. such as port 26 of FIG. 2 or valve 48 of FIG. 13G). Alternatively, the balloon may be self-sealing (similar to self-sealing tires), also allowing inflation/deflation of the balloon using a needle that pierces the stomach wall and the balloon.

A section of reinforcing and/or ingrowth-promoting material 15 (FIG. 6) may be optionally placed between serosal and/or mucosal tissue layers that are positioned in contact with one another. The material may be a synthetic or non-synthetic mesh, porous material, slotted material, or any other material through which adhesions will form or onto which tissue will grow. Examples include, but are not limited to, polypropylene, materials sold under the trade names Goretex or Dacron, or tissue graft material such as the Surgisis material sold by Wilson Cook Medical, Inc. The material may be treated with tissue-ingrowth promoting substances such as biologics. If such material is used, the adhesions that form between the serosal tissue layers will pass through and/or onto the interstices of the material and serve to reinforce the bond between the tissue layers. The material may further cause some mechanical abrasion of the adjacent tissue, creating additional scar tissue that would further reinforce the strength of the opposed tissue.

If adhesion of adjacent mucosal tissue surfaces is desired, modification of the interior tissue surface may further be needed in order to optimize adhesion of opposed regions of internal stomach tissue. In particular, it is believed that better adhesion of the interior wall surfaces may be achieved when a portion of the mucosal layer of tissue lining the stomach interior is removed, such that the tissue surfaces sutured in apposition to one another are serosal, sub-mucosal or muscularis layers. It is believed that opposed layers of mucosal tissue do not adhere together as well as opposed layers of serosal, sub-mucosal, or muscularis tissue. Surface modification methods for promoting such tissue adhesion include cutting, ablating (using RF, laser, or chemical ablation) or abrading the mucosal surface within the stomach as indicated by dashed lines. This modification is ideally performed before the folds are placed in apposition. Depending on the depth to which cutting, ablation or abrasion is performed, the sub-mucosal, musclaris, or serosal layer beneath the mucosal layer is exposed. This allows the exposed regions of tissue to be placed in apposition and causes the opposed surfaces to tightly adhere over time.

Figure 9:
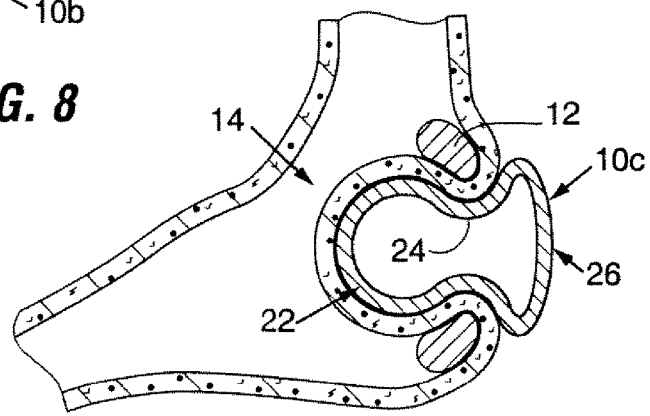
FIG. 9 is a cross-section view of a stomach illustrating positioning of an obstructive implant having an alternative shape.

Although the implants shown in FIGS. 2-6 are illustrated as being spherical, various other configurations may be used. For example, an alternate implant 10a shown in FIG. 7 may include a recess 16 along its surface such that the portion of the stomach wall W following the contour of recess 16 creates a form of pouch or reservoir 18 in the stomach within which food may accumulate. An elongate implant 10b of the type shown in FIG. 8 may be used to form an elongate restriction 20 while greatly reducing the effective volume of the stomach. FIG. 9 shows an implant 10c having a modified hourglass configuration including an obstructive portion 22 that functions to bulge the stomach wall inwardly as described in connection with earlier embodiments. A neck 24 extending from the obstructive portion 22 connects with a base portion 26 that helps to distribute forces imparted against the stomach W and prevents tissue erosion and/or migration of the implant. As shown in the figure, the retention band 12 preferably seats against the stomach tissue surrounding the neck 24.

Many other shapes beyond those shown in this application may be used for the implant (such as for accommodating the shape of the anatomy, or for creating a restriction or obstruction of a particular size/shape), without departing from the scope of the present invention.

There are likewise many suitable structures and materials useful for the implant. Some structures and materials are shown and described herein, although again many others may be used without exceeding the scope of the present invention.

For example, the implant may be an elastic or inelastic balloon that is implantable in a deflated state and then inflated within the body using a gas or liquid. A balloon of this type may include a port such as port 26 shown in FIG. 2. During use an inflation needle may be introduced into the stomach, used to pierce the stomach wall, and then passed into the port 26. The needle may be used to introduce inflation medium into the balloon, or to deflate the balloon if adjustments in balloon size are needed. Alternatively, the balloon may be self-sealing (along the lines of puncture-proof or self-sealing tires), also allowing inflation/deflation of the balloon using a needle that pierces the stomach wall and the balloon. This latter embodiment is advantageous in that it does not necessitate a particular orientation for the balloon as would be needed to orient an inflation port for receipt of an inflation needle.

Figure 10:
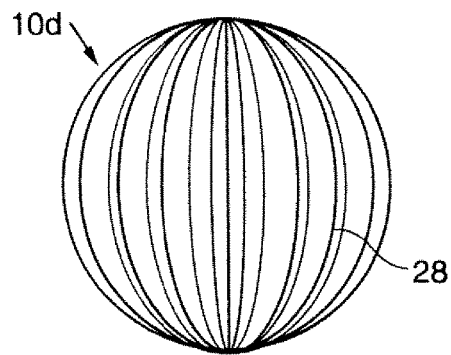
Figure 11:
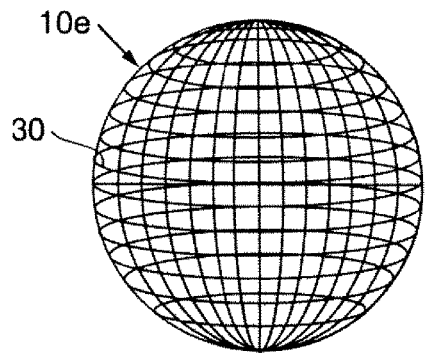
Figure 12A:
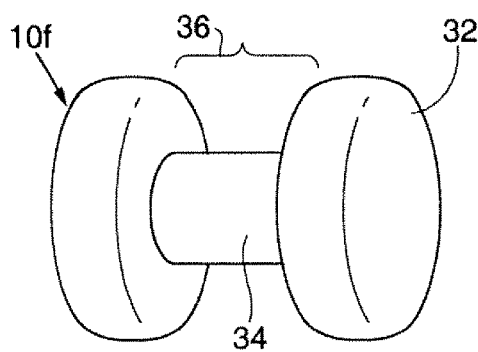
Figure 12B:
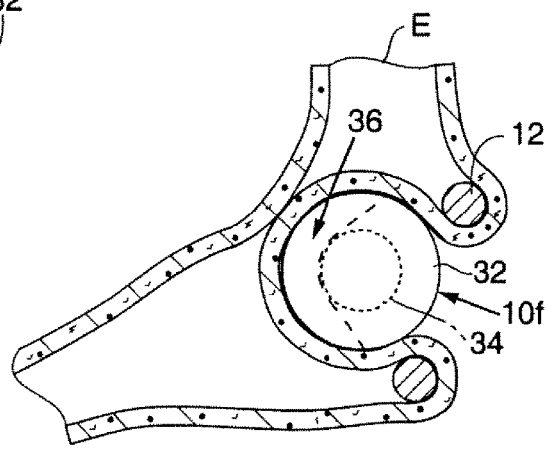
FIG. 12B illustrates the implant of FIG. 12A positioned in the stomach.

Other configurations besides balloons are also suitable for the implant. The implant 10*d* may have fluted walls 28 as shown in FIG. 10, or it may be formed of a mesh 30 as shown in FIG. 11. These implants 10*d*, 10*e* may be self-expanding or they may be provided in a fully expanded form. The implant 10*f* of FIG. 12A includes a pair of plates 32 separated by a neck 34. When positioned as shown in FIG. 12B, a portion of the stomach wall W caves into the gap 36 between the plates 32, creating a flow path for food moving from the esophagus E into the stomach. The amount of restriction provided by the implant 10*f* may be selected by selecting a suitable length or width for the neck 34.

The implant need not be a hollow structure, but could instead be entirely solid.

The implant may be implanted endoscopically using tools passed into the stomach via the esophagus. According to the endoscopic approach, the implant is inserted into the stomach and then passed through an opening formed in the stomach wall. Alternatively, a laparoscopic method may be used to pass the implant into the abdominal cavity through incisions or trocar punctures in the skin. The implant may also be introduced using an open surgical approach. In both the laparoscopic and surgical procedures, the retention band 12 is preferably introduced endoscopically into the stomach.

Figure 13A:
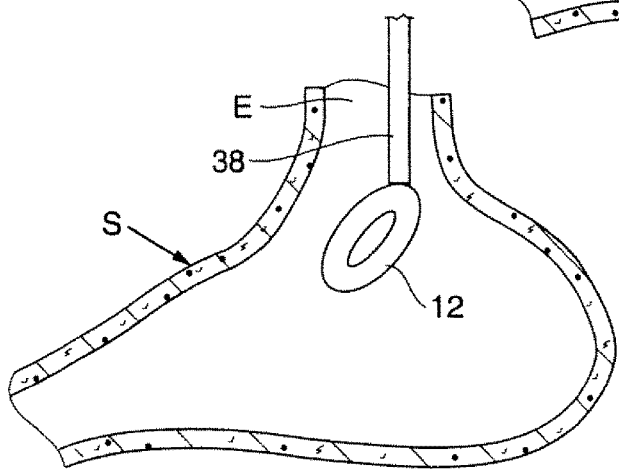
FIGS. 13A through 13F are a sequence of drawings illustrating endoscopic implantation of an obstructive implant.
Figure 13B:
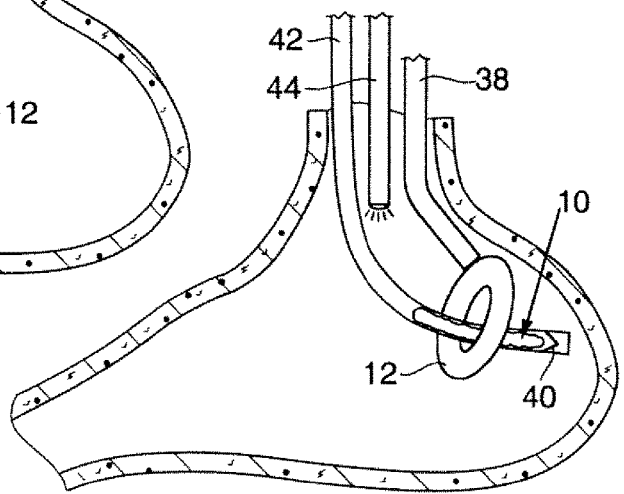

FIGS. 13A through 13F illustrate one method of positioning an inflatable implant using an endoscopic approach. Referring to FIG. 13A, retention band 12 is inserted down the esophagus into the stomach using an endoscopic instrument 38. Next, the implant 10 is passed into the stomach and through the retention band 12 as shown in FIG. 13B. Implant 10 is preferably compressed within a tubular instrument 40 having a tissue-piercing distal end. The instrument 40 may be telescopically disposed within a tubular sheath 42 to prevent the instrument from inadvertently nicking surrounding tissue. Although not shown, an inflation tube extends through the instrument 40 and sheath 42 and is coupled to an inflation port of the implant. An endoscope 44 is used to monitor the procedure.

Figure 13C:
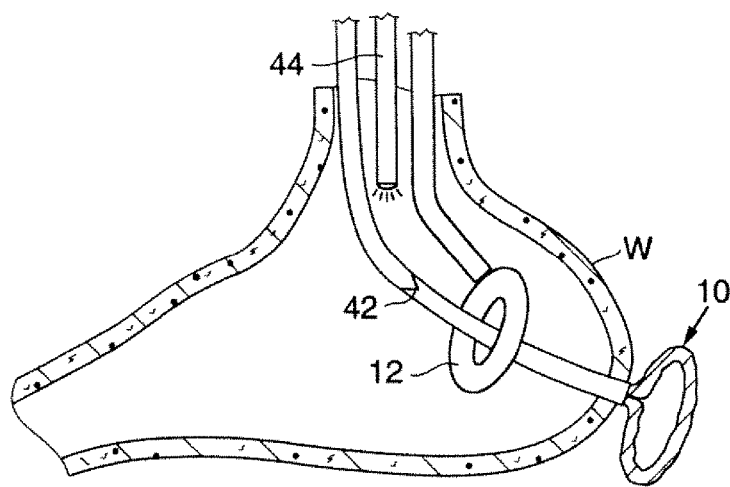

Referring to FIG. 13C, the tissue-piercing instrument 40 is extended from its sheath and used to pierce through the stomach wall W at a desired implant location. The implant 10 is released from the instrument 40 and partially inflated by passing inflation medium through the inflation tube. The tissue-piercing instrument 40 and its sheath 42 may be removed from the stomach, leaving the inflation tube 46 (FIG. 13D) behind.

Figure 13D:
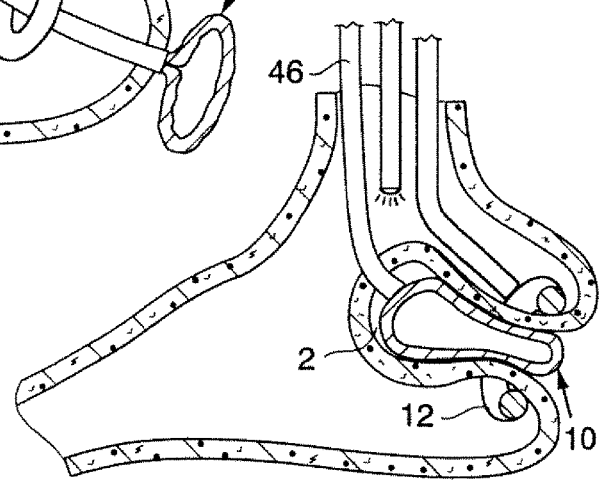
Figure 13E:
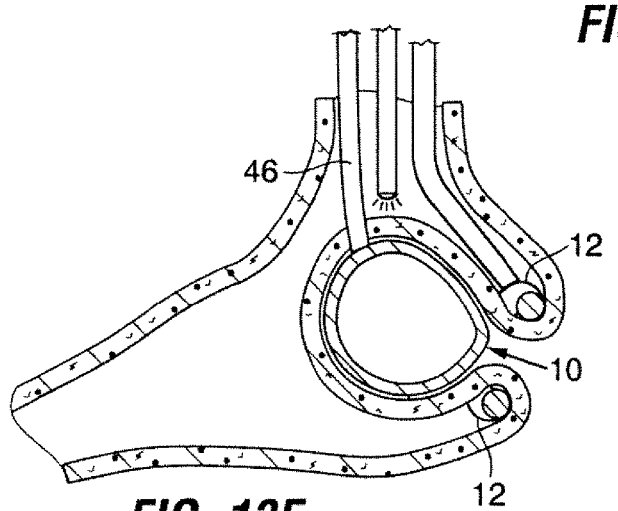
Figure 13F:
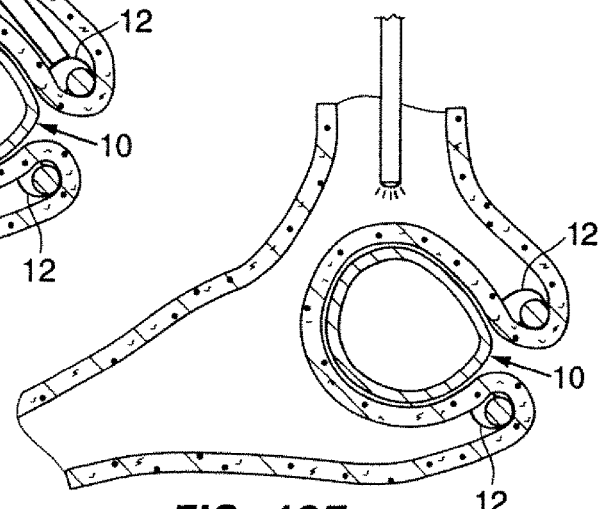

Next, tension is applied to the inflation tube 46 to pull the implant 10 towards the stomach so as to create the pocket 2. This step draws the implant 10 and the surrounding stomach wall through the retention band 12 as shown in FIG. 13D. Once a sufficient amount of tissue has been drawn through the retention band, the implant is inflated to the desired size as shown in FIG. 13E. The inflation tube 46 is detached from the implant 10 and the endoscopic instrument 38 is detached from the retention band 12, leaving the implant in place as shown in FIG. 13F. The hole formed in the stomach wall may be closed using sutures or a sealable gel that solidifies when placed into contact with the tissue.

Referring to FIG. 13G, it should be noted that the implant may include an inflation valve 48 that is left extending through the stomach wall. The valve 48 allows for post-implant size adjustments by allowing inflation medium to be added to or removed from the balloon using an inflation tube passed through the esophagus and attached to the valve. If removal of the balloon is required, the valve may be grasped using endoscopic instruments to draw the balloon back into the stomach and out the esophagus. The valve may be surrounded by a seal to prevent movement of stomach contents into the abdominal space outside the stomach. A gel of a type that will solidify when placed into contact with the stomach surface may be used for this purpose.

The retention band 12 may take alternate forms or be replaced altogether using other types of structures that help to capture the implant 10 in the pocket 2 at the implant site. FIG. 14 illustrates that the cross-sectional area of the restrictive band 12*a* may be large relative to the size of the implant so as to diffuse the forces imparted on the region of stomach wall captured between the band 12*a* and the implant 10 and to thereby prevent erosion of, or damage to, the stomach tissue. FIG. 15 illustrates that a large surface-area retention liner 12*b* may alternatively be used so as to distribute forces over a broader surface. Referring to FIG. 16, the restriction ring 12*c* and implant 10 may be coupled together by an inflation tube 50 extending through the stomach wall. A valve 52 is fluidly coupled to the tube 50 and allows for introduction/removal of inflation medium using an inflation needed passed into the stomach. The valve 52 and tube 50 facilitate explantation of the implant using a grasping instrument inserted through the esophagus and into the stomach.

The retention band itself may be inflatable. Referring to FIG. 17B, the retention band may include separate inflatable chambers 54*a*, 54*b* each having an inflation port 56*a*, 56*b*. The chambers 54*a*, 54*b* are joined together to form an annular band. The upper chamber 54*a* may be shaped to form a channel 58 for passage of food, as shown in FIG. 17B.

Figure 18:
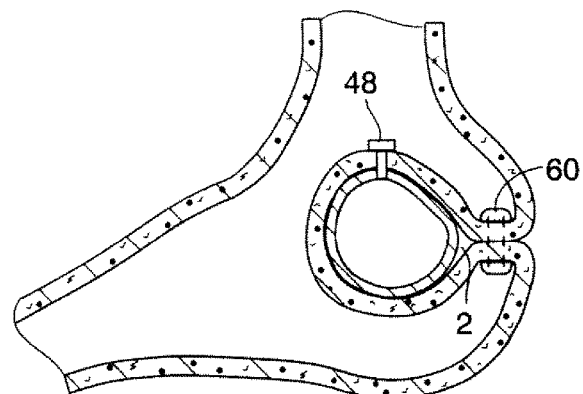

FIG. 18 illustrates that the retention band may be eliminated entirely. As shown, after the implant 10 is pulled against the stomach wall W, stomach tissue adjacent to the pocket 2 can be fastened together using pledgets 60 (or sutures, staples, clips or other means). Over time, a physiological response will cause the regions of serosal tissue held in contact with one another to bond together, thereby retaining the implant in the pocket 2.

Figure 19:
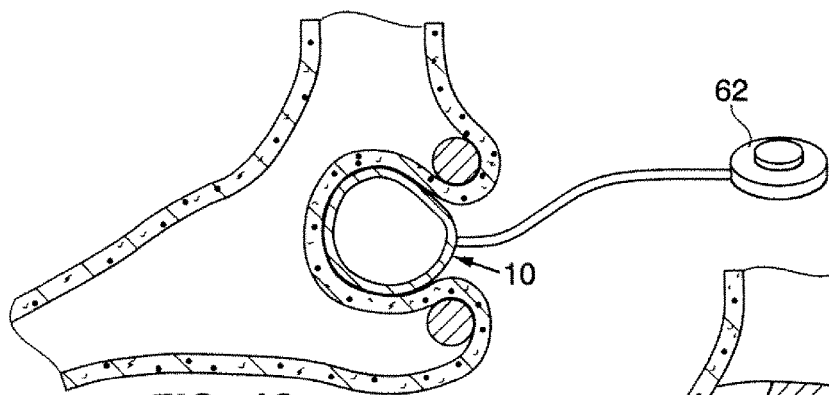
FIG. 19 illustrates an obstructive implant having a subcutaneous inflation port.

Referring to FIG. 19, inflatable implant 10 may be tethered to an inflation port 62 positioned within a subcutaneous pocket in the body. If needed following implantation, an inflation needle may be inserted through the patient's skin and into the inflation port 62 to increase or decrease the amount of inflation medium within the implant.

Figure 20:
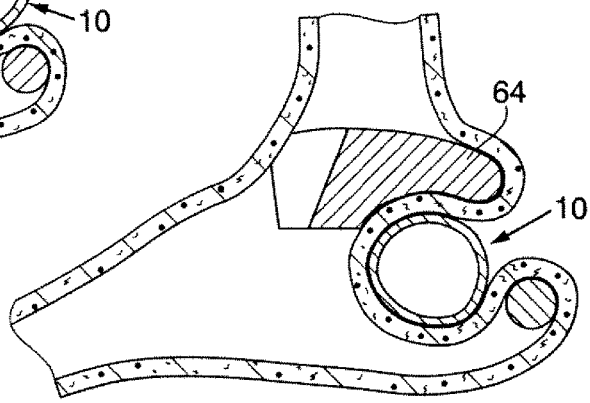
FIGS. 20 and 21 illustrate use of obstructive implants to facilitate retention of other obesity-controlling devices within the stomach.
Figure 21:
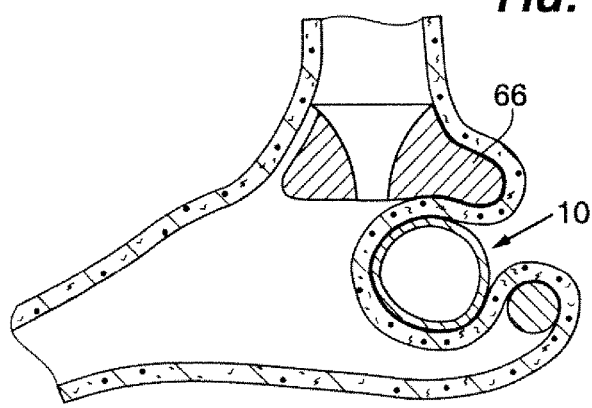

Referring to FIGS. 20 and 21, it should be noted that while the implant 10 may itself provide restriction and/or obstruction, the implant 10 may also be used to prevent migration of a restrictive and/or obstructive device positioned inside the stomach. For example, device 64 of FIG.

20 or device 66 of FIG. 21 may be positioned in the proximal stomach and seat against the portion of the stomach wall that protrudes inwardly as a result of implant 10.

Components of the type described herein may be supplied individually or as systems which may include various combinations of components such as implants (e.g. implant 10), retention devices (e.g. band 12), implantation instruments, and/or instructions for use. If included, instructions for use may include instructions instructing a user to implant the implant using methods such as any of those described above. For example, the instructions may instruct the user to create an inward protrusion in the stomach wall such as by positioning an instrument or the implant against an exterior surface of the stomach wall. The instructions may further instruct the user to position the retention device in a manner that at least partially retains the protrusion in the wall and that thus captures implant within the protrusion, externally of the stomach. In some embodiments where a retention band is provided, the instructions for use may instruct the user to encircle a portion of the protrusion in the wall with the retention band. The instructions may instruct the user as to laparoscopic, endoscopic, and/or open surgical approaches such as those described above.

Various components and methods have been described herein. These embodiments are given by way of example and are not intended to limit the scope of the present invention. It should be appreciated, moreover, that the various features of the embodiments that have been described might be combined in various ways to produce numerous additional embodiments.

What is claimed is:

1. A method of positioning an implant relative to a stomach, comprising:
    inserting an implant, in a collapsed configuration, through an esophagus and into the stomach;
    passing the implant through a stomach wall from an interior of the stomach to an exterior of the stomach;
    after passing the implant through the stomach wall, transforming the implant from the collapsed configuration to an expanded configuration; and
    forming an inward protrusion of the stomach wall, with the implant positioned adjacent the exterior of the stomach and within the inward protrusion.

2. The method of claim 1, further comprising inserting a band through the esophagus and into the stomach.

3. The method of claim 2, further comprising passing the implant through the band.

4. The method of claim 1, further comprising, after transforming the implant from the collapsed configuration to the expanded configuration, pulling the implant against an exterior of the stomach wall to create the inward protrusion of the stomach wall.

5. The method of claim 4, further comprising, after pulling the implant against the stomach wall to create the inward protrusion, transforming the implant to a further expanded configuration.

6. The method of claim 1, wherein the implant includes an elongated shape.

7. The method of claim 1, wherein the step of transforming the implant from the collapsed configuration to the expanded configuration includes inflating the implant with an inflation medium.

8. The method of claim 1, wherein the step of transforming the implant from the collapsed configuration to the expanded configuration includes allowing the implant to self-expand.

9. A method of positioning an implant relative to a stomach, comprising:
    positioning a retention device in an interior of the stomach;
    positioning an implant exterior to the stomach and adjacent to an exterior of a stomach wall;
    moving the implant against the exterior of the stomach wall to form an inward protrusion of the stomach wall; and
    expanding the implant from a first configuration to a second configuration.

10. The method of claim 9, wherein moving the implant against the exterior of the stomach wall to form the inward protrusion includes passing at least a portion of the inward protrusion through the retention device.

11. The method of claim 9, wherein positioning the implant exterior to the stomach includes passing the implant through an esophagus, into the stomach, and through the stomach wall from the interior of the stomach to the exterior of the stomach.

12. The method of claim 9, wherein expanding the implant occurs partially before moving the implant against the exterior of the stomach wall to form the inward protrusion and partially after moving the implant against the exterior of the stomach wall to form the inward protrusion.

13. The method of claim 9, wherein the retention device is expandable.

14. The method of claim 9, wherein the implant includes a port configured to receive an inflation device.

15. The method of claim 9, wherein the implant includes a self-sealing material.

16. A method of positioning an implant relative to a stomach, comprising:
    passing an implant transorally and through a wall of the stomach from an interior of the stomach to an exterior of the stomach;
    expanding the implant; and
    forming an inward protrusion of the stomach, with the implant positioned exterior to the stomach and at least partially within the inward protrusion.

17. The method of claim 16, further comprising positioning a retention device in the interior of the stomach in contact with the inward protrusion.

18. The method of claim 16, wherein expanding the implant includes inflating the implant with an inflation medium.

19. The method of claim 16, wherein expanding the implant includes allowing the implant to self-expand.

* * * * *